(12) United States Patent
Harreld

(10) Patent No.: US 11,903,813 B2
(45) Date of Patent: Feb. 20, 2024

(54) INTRAOSSEOUS SCREW WITH CORTICAL WINDOW AND SYSTEM AND METHOD FOR ASSOCIATING SOFT TISSUE WITH BONE

(71) Applicant: Kevin L. Harreld, Louisville, KY (US)

(72) Inventor: Kevin L. Harreld, Louisville, KY (US)

( * ) Notice: Subject to any disclaimer, the term of this patent is extended or adjusted under 35 U.S.C. 154(b) by 401 days.

(21) Appl. No.: 16/847,768

(22) Filed: Apr. 14, 2020

(65) Prior Publication Data
US 2020/0323622 A1      Oct. 15, 2020

Related U.S. Application Data

(60) Provisional application No. 62/834,290, filed on Apr. 15, 2019.

(51) Int. Cl.
*A61B 17/04* (2006.01)
*A61F 2/08* (2006.01)

(52) U.S. Cl.
CPC ........ *A61F 2/0811* (2013.01); *A61B 17/0401* (2013.01); *A61B 2017/044* (2013.01);
(Continued)

(58) Field of Classification Search
CPC ...... A61B 2017/0409; A61B 2017/044; A61B 2017/0445; A61B 2017/0464; A61F 2002/0858; A61F 2002/0864
See application file for complete search history.

(56) References Cited

U.S. PATENT DOCUMENTS

| | | | |
|---|---|---|---|
| 4,997,433 A * | 3/1991 | Goble | A61F 2/0811 606/62 |
| 5,100,417 A * | 3/1992 | Cerier | A61B 17/0401 606/232 |

(Continued)

FOREIGN PATENT DOCUMENTS

| | | |
|---|---|---|
| EP | 1332729 A1 | 8/2003 |
| WO | 2013159760 A1 | 10/2013 |

(Continued)

OTHER PUBLICATIONS

"Twist & Triple Twist Peek Screw-In Suture Anchors," parcusmedical.com. Mar. 18, 2017. https://web .archive.org/web/20170318160848/http://www.parcusmedical.com/Products (Click Product Catalog).
Amouyel, Thomas et al. "Arthroscopic Biceps Tenodesis Using Interference Screw Fixation in the Bicipital Groove," ncbi.nlm.nih.gov. Accessed: May 30, 2019. https://web .archive.org/web/20190530023306/https://www.ncbi.nlm.nih.gov/p mc/articles/PMC5798995/ US National Library of Medicine, National Institutes of Health. Arthroscopy Techniques: 6(5) e1953-e1957, Oct. 2017 (Published online: Oct. 23, 2017).

(Continued)

*Primary Examiner* — Alexander J Orkin
(74) *Attorney, Agent, or Firm* — Stites & Harbison, PLLC; Jeffrey A. Haeberlin; Gary N. Stewart

(57) ABSTRACT

An intraosseous screw for deposit into a bone structure and retaining a soft tissue therein. The intraosseous screw includes a body and a retention member. The body defines an axial cavity in which soft tissue can be deposited and a window that permits the soft tissue to contact the bone structure in which the intraosseous screw is deposited. The retention member is positioned within the axial cavity and at least partially defines an opening through which a suture connected to soft tissue can pass to facilitate anchoring of the soft tissue within the axial cavity. The intraosseous screw can be combined with a passing suture, driver, and/or peg to provide a system for associating soft tissue with a bone structure. The intraosseous screw can be utilized in a method in which soft tissue is deposited into a bone structure after the interosseous screw is fully deposited in the bone structure.

20 Claims, 12 Drawing Sheets

(52) U.S. Cl.
CPC ............. *A61B 2017/0409* (2013.01); *A61B 2017/0414* (2013.01); *A61B 2017/0445* (2013.01); *A61B 2017/0464* (2013.01); *A61F 2002/0841* (2013.01); *A61F 2002/0858* (2013.01)

(56) References Cited

U.S. PATENT DOCUMENTS

| | | | | |
|---|---|---|---|---|
| 5,151,104 | A * | 9/1992 | Kenna | A61F 2/0811 606/328 |
| 5,505,735 | A * | 4/1996 | Li | A61F 2/0811 606/232 |
| 5,632,748 | A * | 5/1997 | Beck, Jr. | A61F 2/0811 606/328 |
| 5,766,250 | A * | 6/1998 | Chervitz | A61B 17/1675 606/232 |
| 5,868,789 | A * | 2/1999 | Huebner | A61B 17/0401 606/232 |
| 5,984,966 | A * | 11/1999 | Kiema | A61F 2/0811 623/13.14 |
| 6,162,234 | A * | 12/2000 | Freedland | A61F 2/0811 606/313 |
| 6,214,007 | B1 | 4/2001 | Anderson | |
| 7,083,647 | B1 | 8/2006 | Sklar et al. | |
| 7,651,528 | B2 | 1/2010 | Montgomery et al. | |
| 8,147,546 | B2 | 4/2012 | Stone et al. | |
| 8,470,037 | B2 | 6/2013 | Re et al. | |
| 8,845,725 | B2 | 9/2014 | Barwood et al. | |
| 9,023,083 | B2 * | 5/2015 | Foerster | A61F 2/0811 606/232 |
| 9,089,415 | B2 | 7/2015 | Brunelle et al. | |
| 9,265,600 | B2 | 2/2016 | Niese et al. | |
| 9,662,107 | B2 * | 5/2017 | Stone | A61B 17/0642 |
| 9,763,719 | B2 | 9/2017 | Snyder et al. | |
| 9,808,298 | B2 | 11/2017 | Stroncek et al. | |
| 9,855,033 | B2 | 1/2018 | Bennett et al. | |
| 9,907,548 | B2 | 3/2018 | Dougherty et al. | |
| 9,913,638 | B2 | 3/2018 | Saliman et al. | |
| 9,931,195 | B2 | 4/2018 | Arai et al. | |
| 9,987,065 | B2 | 6/2018 | De Lavigne Sainte Suzanne | |
| 2002/0007182 | A1 * | 1/2002 | Kim | A61F 2/0811 606/53 |
| 2002/0052630 | A1 * | 5/2002 | Morgan | D04C 1/12 606/232 |
| 2003/0065390 | A1 * | 4/2003 | Justin | A61F 2/0811 606/65 |
| 2003/0105489 | A1 * | 6/2003 | Eichhorn | A61F 2/0811 606/232 |
| 2003/0171811 | A1 * | 9/2003 | Steiner | A61L 27/386 623/13.17 |
| 2005/0283158 | A1 * | 12/2005 | West, Jr. | A61B 17/863 606/907 |
| 2007/0203498 | A1 * | 8/2007 | Gerber | A61B 17/0401 606/328 |
| 2007/0225719 | A1 * | 9/2007 | Stone | A61B 17/0401 606/232 |
| 2008/0009904 | A1 * | 1/2008 | Bourque | A61B 17/0401 606/232 |
| 2008/0154313 | A1 * | 6/2008 | Berberich | A61B 17/0401 606/301 |
| 2008/0275469 | A1 * | 11/2008 | Fanton | A61B 17/0487 606/232 |
| 2009/0076544 | A1 * | 3/2009 | DiMatteo | A61B 17/0401 606/232 |
| 2009/0306711 | A1 * | 12/2009 | Stone | A61B 17/0469 606/232 |
| 2009/0312794 | A1 * | 12/2009 | Nason | A61B 17/0485 606/232 |
| 2010/0063541 | A1 * | 3/2010 | Brunelle | A61F 2/0811 606/301 |
| 2011/0264140 | A1 * | 10/2011 | Lizardi | A61B 17/0401 606/232 |
| 2011/0270306 | A1 * | 11/2011 | Denham | A61B 17/06166 606/228 |
| 2012/0059384 | A1 * | 3/2012 | Fan | A61F 2/0805 606/104 |
| 2012/0179199 | A1 * | 7/2012 | Hernandez | A61B 17/0485 606/232 |
| 2013/0060280 | A1 * | 3/2013 | Wolf | A61B 17/0401 606/232 |
| 2014/0058461 | A1 | 2/2014 | Black | |
| 2015/0272567 | A1 * | 10/2015 | Feezor | A61B 17/0485 606/232 |
| 2016/0030032 | A1 * | 2/2016 | Dougherty | A61B 17/0401 606/232 |
| 2016/0113643 | A1 * | 4/2016 | Diduch | A61F 2/0805 606/232 |
| 2017/0189007 | A1 | 7/2017 | Burkhart et al. | |
| 2019/0343507 | A1 * | 11/2019 | Chavan | A61B 17/0401 |

FOREIGN PATENT DOCUMENTS

| | | |
|---|---|---|
| WO | 2017032901 A1 | 3/2017 |
| WO | 2017142142 A1 | 8/2017 |

OTHER PUBLICATIONS

"Quattro Bolt Tenodesis Screw," zimmerbiomet.com. May 30, 2019. https://web.archive.org/web/20190530025410/https://www.zimmerbiomet.com /medical-professionals/sports-medicine/product/quattro-bolt-tenodesis-screw.html.

"iFix Interference Screw," zimmerbiomet.com, May 30, 2019. https://web.archive.org/web/20190530030002/https://www.zimmerbiomet.com /medical-professionals/sports-medicine/product/ifix-screw1.html.

"BOIS Peek Interference Screw," seohancare.com. May 30, 2019. https://web.archive.org/web/20190530030703/http://www.seohancare.com/ho me/bbs/board.php?bo_table=pro&wr_id=26&page=2.

\* cited by examiner

INTRAOSSEOUS SCREW WITH CORTICAL WINDOW AND SYSTEM AND METHOD FOR ASSOCIATING SOFT TISSUE WITH BONE

CROSS-REFERENCE TO RELATED APPLICATIONS

This application claims the benefit of U.S. Provisional Patent Application No. 62/834,290, filed Apr. 15, 2019, the entire disclosure of which is hereby incorporated by reference.

BACKGROUND OF THE INVENTION

1. Field of the Invention

The present invention pertains to the field of soft tissue surgical repair using an intraosseous screw. In particular, the invention relates to an intraosseous screw including a cortical window through which soft tissue can interface with an adjacent bone structure, and a system and a method for associating soft tissue with bone utilizing the intraosseous screw.

2. Background Art

In the medical field, numerous surgical procedures involve associating a target soft tissue with a target bone structure. Two such procedures include the fixation of ligament reconstruction grafts and the repair or transfer of musculotendinous units. Traditionally, in such procedures, a surgically created bone tunnel is first established within a target bone. The target soft tissue and an intraosseous screw are subsequently deposited into the created bone tunnel, such that the soft tissue is interposed between the bony cortex of the target bone structure and an intraosseous screw. Following such deposit, the intraosseous screw is then manipulated to set the threading of the intraosseous screw within the bony cortex and maintain the soft tissue in the desired orientation within the bone tunnel.

However, a number of problems can arise during such procedures due to the interposition of the soft tissue between the intraosseous screw and bony cortex. For instance, the soft tissue can act as a physical barrier which compromises the purchase of the threading of the intraosseous screw on the bony cortex. Further, initiating deposit of the intraosseous screw into a bone tunnel containing soft tissue can be difficult, and tunnel widening often occurs as a result of repeated attempts to gain the necessary screw purchase required for advancement of the intraosseous screw into the bone tunnel. Additionally, as the soft tissue occupies a certain amount of volume within the bone tunnel, selecting the correct intraosseous screw size needed to provide the optimal interface between the intraosseous screw, soft tissue, and bony cortex can be difficult. As a result, mismatch in sizing between the soft tissue, intraosseous screw, and bony cortex is common. Selecting an undersized intraosseous screw can result in slippage of the soft tissue from the bone tunnel and overall failure of the procedure. Conversely, selecting an oversized intraosseous screw can result in an overly tight mismatch which causes the soft tissue to wrap around the intraosseous screw as it manipulated to set the threading within the bony cortex, thus leading to inaccurate tensioning of the soft tissue.

BRIEF SUMMARY OF THE INVENTION

The invention is an intraosseous screw which can be deposited into a target bone structure and utilized to anchor a soft tissue to the target bone structure during surgical repair.

The intraosseous screw includes a body and a retention member. The body defines a longitudinal axial cavity in which a soft tissue can be deposited and a window that permits soft tissue deposited within the axial cavity to contact the target bone structure in which the intraosseous screw is deposited. The retention member is positioned within the axial cavity and at least partially defines an opening through which a suture connected to the soft tissue can pass to facilitate anchoring of the soft tissue within the axial cavity.

In one embodiment, the window extends from an open proximal end towards a closed distal end of the body, such that a rim defined by the proximal end is continuous (i.e., broken) and a portion of the window is not enclosed by the body. Alternatively, in another embodiment, the rim may be continuous (i.e., unbroken), such that the window is fully enclosed by the body. To provide a passageway wide enough to facilitate contact between the soft tissue deposited within the axial cavity and the target bone structure in which the intraosseous screw is deposited, the window is preferably approximately one-fourth to approximately one-half of the circumference of the body. To ensure the full length of the window can be utilized by soft tissue to engage the target bone structure, the retention member is preferably positioned within the axial cavity below the window. In some embodiments, the retention member is defined by the body and extends upwardly from a base of the axial cavity towards the proximal end.

To facilitate deposit of the intraosseous screw into the target bone structure, the body has a threaded exterior surface and an interior surface configured to mate with a driver designed to deposit the intraosseous screw into the target bone structure. In some embodiments, the interior surface can include a first portion which is configured to mate with a shaft of the driver and a second portion which defines a circumferential shelf surrounding the retention member and serves as a stopper defining the outer limit to which the shaft can be inserted into the axial cavity. In some embodiments, the interior surface of the body is configured to mate with drivers having a hexagonally shaped shaft.

The intraosseous screw can be held in association with the driver, such that a distal end of the shaft of the driver is already inserted within the axial cavity 15 prior to use the intraosseous screw, using a passing suture. To hold the driver and intraosseous screw in association with each other, the passing suture can be passed through the opening at least partially defined by the retention member so that opposing ends of the passing suture are positioned outside of the axial cavity. The distal end of the driver can then be inserted into the axial cavity of the intraosseous screw and the passing suture subsequently wrapped or tied around the driver to prevent disassociation of the driver and the intraosseous screw. In some embodiments, the driver may include a cannulated handle and shaft to permit passage of the passing suture through the interior of the driver. In addition holding the intraosseous screw and the driver in association with one another, the passing suture may also be utilized to guide the suture connected to soft tissue through the opening at least partially defined by the retention member.

The axial cavity provided within the intraosseous screw enables the intraosseous screw to be fully deposited within the target bone structure prior to insertion of the soft tissue into the target bone structure and prior to association of the soft tissue with the intraosseous screw. In this way, the intraosseous screw of the present invention serves to alleviate or minimize the above-identified problems associated with interposing the soft tissue between the target bone structure and intraosseous screw. Once the intraosseous screw is fully deposited within the target bone structure, the suture connected to the soft tissue can be guided through the opening at least partially defined by the retention member to draw the soft tissue into the axial cavity. In some embodiments, the retention member may include a slot configured to receive the suture connected to the soft tissue.

After passing through the opening at least partially defined by the retention member, the suture connected to the soft tissue can be passed back through the soft tissue and tied thereto to maintain the soft tissue within the axial cavity. In some embodiments, the intraosseous screw may further include a secondary retention member to which the suture connected to the soft tissue can be tied to in addition to or in place of being tied to the soft tissue. To urge the soft tissue towards the window and promote contact between the soft tissue and the bone structure in which the intraosseous screw is deposited, a peg can be inserted into the axial cavity. In some embodiments, the interior surface of the body of the intraosseous screw defines a recess within the axial cavity configured to receive a portion of the peg.

Accordingly, in another aspect, the present invention is directed to systems and methods for associating a soft tissue with a target bone structure.

BRIEF DESCRIPTION OF THE SEVERAL VIEWS OF THE DRAWINGS

These and other features, aspects, and advantages of the present invention will become better understood with regard to the following description, appended claims, and accompanying drawings where:

DETAILED DESCRIPTION OF EXEMPLARY EMBODIMENTS OF THE INVENTION

Figure 1:
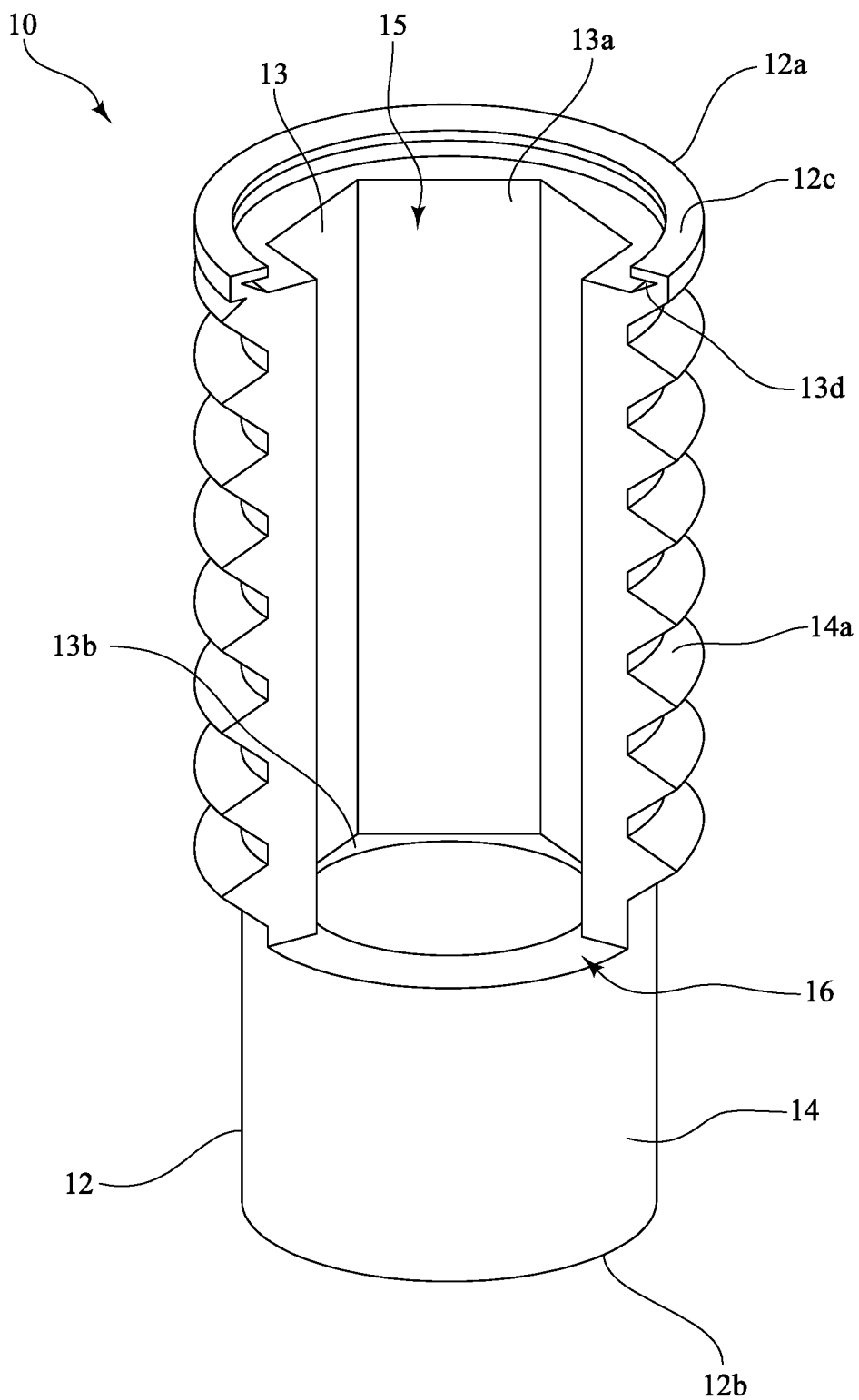
FIG. 1 is a perspective view of an exemplary intraosseous screw made in a accordance with the present invention.

The details of one or more embodiments of the presently-disclosed subject matter are set forth below and in attachments to this document. Modifications to embodiments described below and in the attachments, and other embodiments, will be evident to those of ordinary skill in the art after a study of the information provided in these attachments. The information provided in these attachments, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims.

FIGS. 1-6 show various views of an exemplary intraosseous screw 10, which can be deposited into a target bone structure 50 and utilized to anchor a soft tissue 60 during surgical repair. As shown in FIGS. 1-6, the intraosseous screw 10 generally includes a body 12 configured to receive a soft tissue 60 and a retention member 20 within the body 12 to which the soft tissue 60 can be anchored to retain the soft tissue 60 within the interior of the intraosseous screw 10. Consistent with traditional intraosseous screws, the body 12 of the exemplary intraosseous screw 10 is shaped such that the intraosseous screw 10 retains a generally cylindrical shape. To facilitate purchase of the intraosseous screw 10 with the bony cortex of a target bone structure 50 once inserted therein, the body 12 includes an exterior surface 14 partially defined by threading 14a. The exemplary intraosseous screw 10 can thus be deposited into the target bone structure 50 in the same or similar manner as intraosseous screws currently known within the art.

Unlike intraosseous screws of known construction, however, the body 12 of the exemplary intraosseous screw 10 of the present disclosure defines an axial cavity 15 which permits deposit of soft tissue 60 into the interior of the intraosseous screw 10 after the intraosseous screw 10 is already deposited within the target bone structure 50. To this end, the axial cavity 15 is longitudinally oriented in the center the intraosseous screw 10, such that the axial cavity 15 extends from a proximal end 12a towards a distal end 12b of the body 12. Entry into the axial cavity 15 is facilitated by way of an inlet, which is defined by a rim 12c. The rim 12c is defined by the proximal end 12a of the body 12 and is positioned opposite of a closed distal end 12b of the body 12. In this exemplary embodiment, the axial cavity 15 substantially extends the length of the body 12, such that the axial cavity 15 extends from the proximal end 12a to a point proximate to the closed distal end 12b of the body 12, as shown in FIGS. 3-6. Of course, the extent to which the axial cavity 15 extends (i.e., the depth of the axial cavity 15) may vary to accommodate different surgical applications and/or soft tissue lengths without changing the principle operation of the intraosseous screw 10.

Referring now specifically to FIGS. 2-6, the retention member 20 is positioned within the axial cavity 15 and can be used in combination with a suture 65 to retain soft tissue 60 within the axial cavity 15 once deposited therein. To this end the, the retention member 20 at least partially defines an opening 22 through which a suture 65 connected to soft tissue 60 can pass to anchor the soft tissue 60 within the axial cavity 15. In this exemplary embodiment, the retention member 20 is positioned at the bottom of the axial cavity 15 below a window 16 defined by the body 12, as further described below. The retention member 20 extends upwardly from a base 13c defined by an interior surface 13 of the body 12 towards the proximal end 12a. In this embodiment, the retention member 20 defines an arc which is enclosed by the base 13c. Thus, in this exemplary embodiment, the retention member 20 and base 13c collectively define the opening 22. Furthermore, in this exemplary embodiment, the retention member 20 is defined by the body 12 of the intraosseous screw 10, such that the retention member 20 and the base 13c are integrally formed. Of course, in alternative embodiments, the retention member 20 and the body 12 may exist as two separate components joined together and still establish an anchoring structure suitable for maintaining the soft tissue 60 within the axial cavity 15. For example, in some embodiments, the retention member 20 alone may define the opening 22.

Referring now specifically to FIGS. 1, 2, 5, and 6, the body 12 also defines a window 16 through which soft tissue 60 deposited within the axial cavity 15 and anchored to the retention member 20 can interface with the target bone structure 50 from the interior of the intraosseous screw 10. In this exemplary embodiment, the window 16 extends from the rim 12c towards the distal end 12b of the body 12. Thus, in this exemplary embodiment, the rim 12c of the body 12 is noncontinuous, such that a portion of the window 16 is not enclosed by the body 12. To ensure the full length of the window 16 can be utilized by soft tissue 60 deposited within the axial cavity 15, the window 16 preferably terminates at a point within the body 12 that is positioned above the retention member 20. To facilitate sufficient contact between soft tissue 60 deposited and retained in the axial cavity 15 and the target bone structure 50 in which the intraosseous screw 10 is deposited, it is generally preferred that the window 16 extend at least approximately three-fourths of the total length of the body 12. In this exemplary embodiment, the window 16 extends approximately three-fourths of the total length of the body 12.

Figure 2:
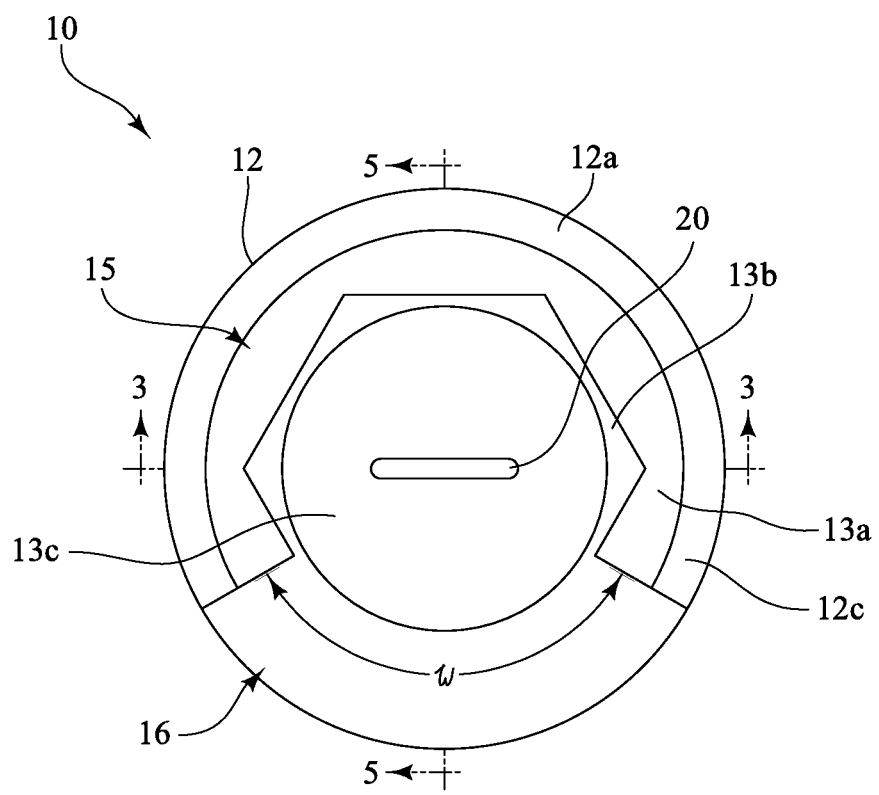
FIG. 2 is a top view of the exemplary intraosseous screw of FIG. 1.
Figure 3:
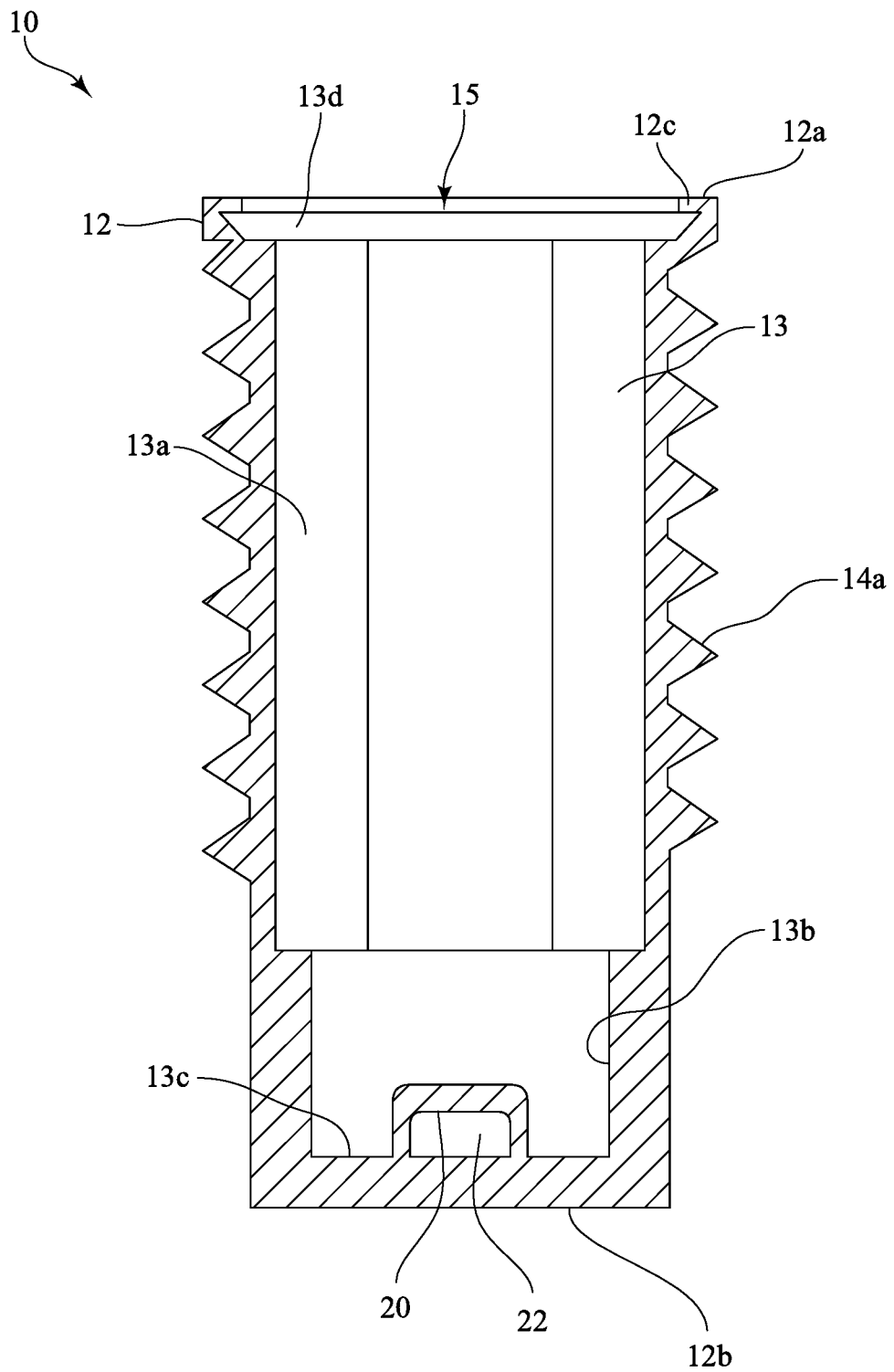
FIG. 3 is a cross-sectional view of the exemplary intraosseous screw of FIG. 2 taken along line 3-3.

Referring specifically to FIGS. 1 and 2, to provide a passageway wide enough to facilitate contact between soft tissue 60 deposited within the axial cavity 15 and the target bone structure 50 without compromising the structural integrity of the intraosseous screw 10, the width, w, of the window 16 is preferably approximately one-fourth to approximately one-half of the overall circumference of the non-threaded portion of the body 12. In this exemplary embodiment, the width, w, of the window 16 is approximately one-fourth of the non-threaded portion of the body 12. Of course, the width, w, of the window 16 may be adjusted based on the materials from which the intraosseous screw 10 is constructed or to accommodate a specific surgical procedure. For instance, the width, w, of the window 16 may be larger in instances where the intraosseous screw 10 is constructed of a metal material, such as titanium, without significantly impacting the structural integrity of the intraosseous screw 10, as compared to instances where the intraosseous screw 10 is constructed of a thermoplastic material, such as polyether ether ketone (PEEK).

As noted above, and referring now to FIGS. 1 and 3-6, in order to facilitate adequate purchase of the intraosseous screw 10 within the target bone structure 50, an exterior surface 14 of the body 12 is partially defined by threading 14a which configured to interface with the bony cortex and direct the intraosseous screw 10 into the target bone structure 50 in response to the application of torque, i.e., the rotation of the intraosseous screw 10 in a rotational direction (e.g., clockwise). In this regard, the intraosseous screw 10 is a self-tapping screw. In this exemplary embodiment, the threading 14a extends coextensively with, and is broken up by, the window 16. Thus, in this exemplary embodiment, the threading 14a extends approximately three-fourths of the body 12 and is defined by a plurality of individual threads. The threading 14a can, however, be adjusted at the time of manufacture with respect to thread angle, thread pitch, and the extent to which the threading 14a extends along the length of the body 12. For instance, in some embodiments, the threading 14a may extend the entire length of the body 12 to further increase purchase of the intraosseous screw 10 with the target bone structure 50. To facilitate alignment with a surgically created bone tunnel and initiate deposit of the threading 14a into the target bone structure, the distal end 12b of the body 12 may, in some embodiments, be tapered. In such embodiments, the tapered distal end 12b may include threading 14a, such that the intraosseous screw 10 can be utilized as a self-drilling screw, thereby potentially eliminating the need for the creation of a bone tunnel prior to screw deposit in certain surgical applications.

Figure 4:
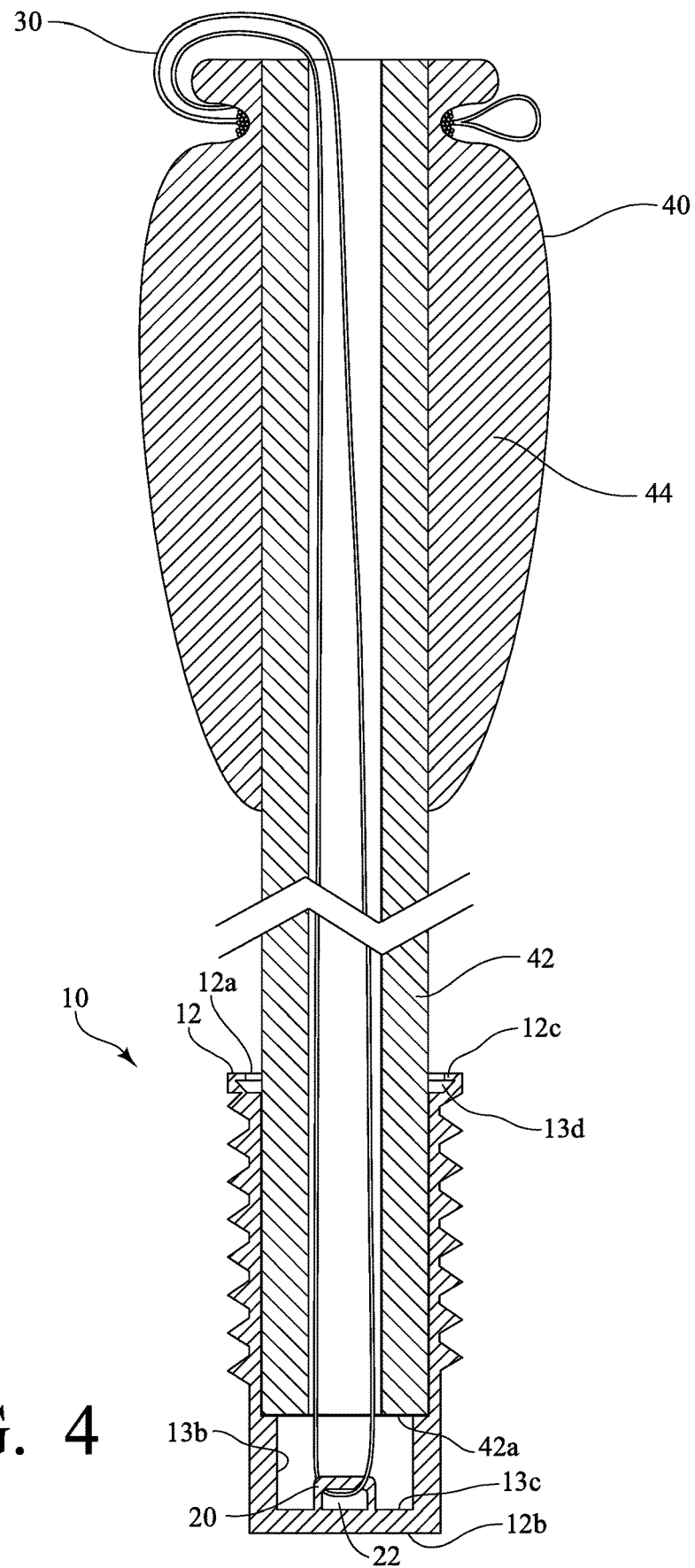
FIG. 4 is a sectional view of the exemplary intraosseous screw of FIG. 3 and a driver, with a passing suture inserted within a axial cavity of the intraosseous screw and extending through the interior of the driver.

Referring now specifically to FIGS. 1-4, to facilitate deposit of the intraosseous screw 10 into the target bone structure 50, the body 12 is configured to receive and mate with a driver 40 designed to drive the intraosseous screw 10 into the target bone structure 50. Specifically, as shown in FIG. 4, the body 12 is configured to receive a distal end 42a of a shaft 42 of the driver 40. To this end, at least a portion of the interior surface 13 of the body 12 is shaped to correspond with the shaft 42 of the driver 40, such that, as the driver 40 is rotated, the intraosseous screw 10, too, is rotated. In this exemplary embodiment, the interior surface 13 of the body 12 is defined by and can be characterized as including: a first portion 13a configured to mate with the shaft 42 of the driver 40 and a first shelf positioned below the rim 12c, the importance of which will be described below; a second portion 13b defining a second, circumferential shelf surrounding the retention member 20; and a third portion, which defines the base 13c identified above. In this exemplary embodiment, the first portion 13a of the interior surface 13 is shaped to mate with a driver 40 having a hexagonally shaped shaft 42. To this end, in this exemplary embodiment, the first portion 13a of the interior surface 13 defines a five-sided wall broken by the window 16, which, in this case, extends coextensively with the first portion 13a of the interior surface 13. The circumferential shelf defined by the second portion 13b of the interior surface 13 serves as a stopper which defines the outer limit to which the shaft 42 can be inserted into the axial cavity 15. Of course, the interior surface 13 may be alternatively designed and still permit entry and subsequent rotation of the shaft 42 of the driver 40 in a manner sufficient to drive the intraosseous screw 10 into the target bone structure 50. For instance, the first portion 13a of the interior surface 13 may be alternatively shaped to receive and mate with shafts 42 of other shapes. In some embodiments, the interior surface 13 may be devoid of the second portion 13b and circumferential shelf defined thereby, such that the first portion 13a of the interior surface configured to mate with the shaft 42 of the driver 40 extends all the way to the base 13c defined by the third portion of the interior surface 13.

Figure 5:
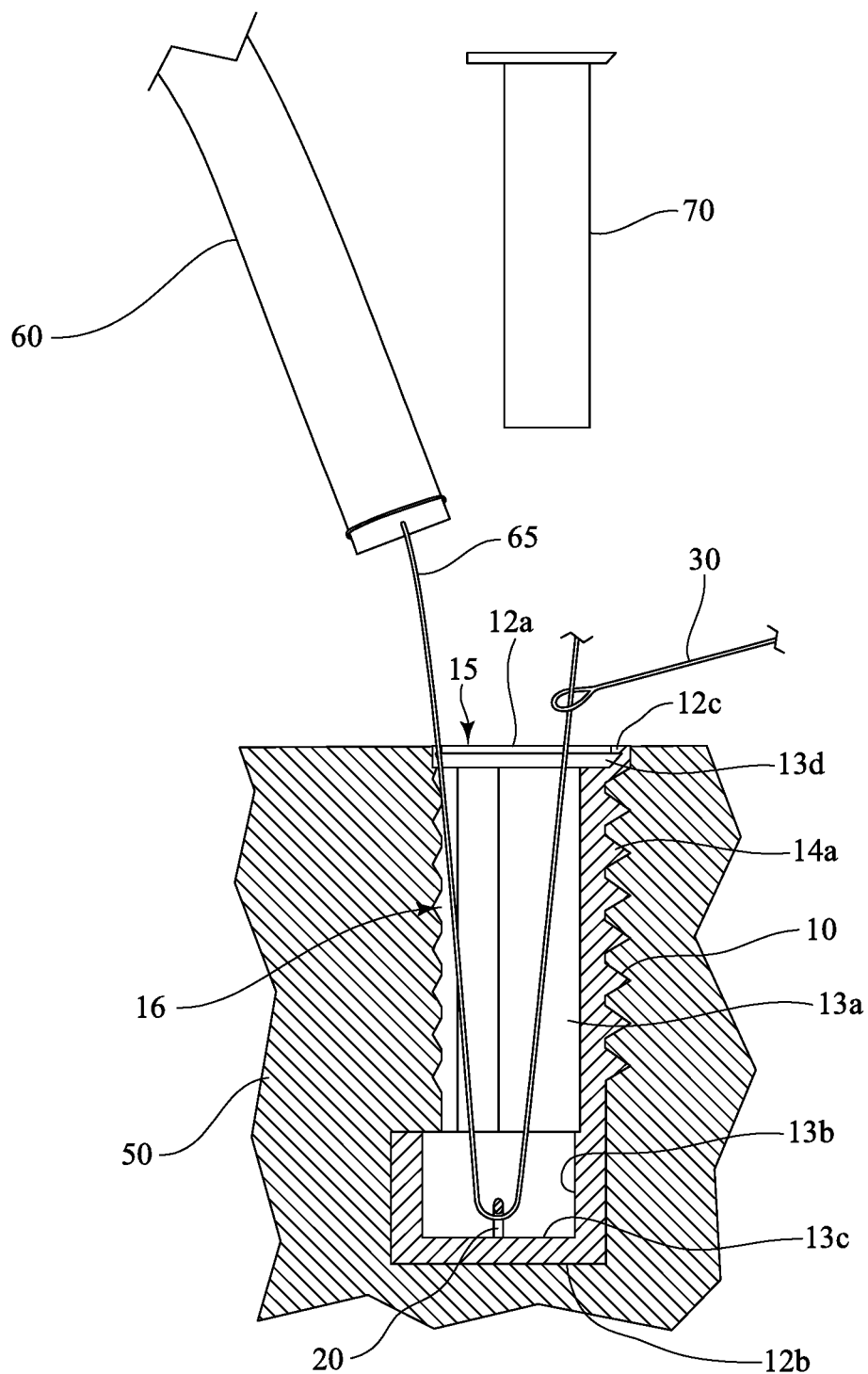
FIG. 5 is another sectional view of the exemplary intraosseous screw of FIG. 2 taken along line 5-5 and deposited within a bone structure, with a suture connected to soft tissue and inserted within the axial cavity of the intraosseous screw and a passing suture and a peg positioned above the axial cavity.

Referring now specifically to FIG. 4, the intraosseous screw 10 can be held in association with the driver 40, such that the distal end 42a of the shaft 42 is already inserted within the axial cavity 15 prior to use of the intraosseous screw 10, using a passing suture 30. In addition to holding the intraosseous screw 10 and driver 40 in association with one another, the passing suture 30 can also be used to guide a suture connected to soft tissue through the opening 22 defined by the retention member 20 and base 13c, as shown in FIG. 5 and further described below. To this end, the passing suture 30 is preferably a looped passing suture. To hold the driver 40 and intraosseous screw 10 in association with each other and provide a guide through the opening 22 for the suture 65 connected to the soft tissue 60, the passing suture 30 is first passed through the opening 22 defined by the retention member 20 and base 13c so that the opposing ends of the passing suture 30 are positioned outside of the axial cavity 15. The distal end 42a of the driver 40 is then inserted into the axial cavity 15 and the opposing ends of the passing suture 30 are wrapped around or tied to the driver 40 in a manner sufficient to prevent the driver 40 and intraosseous screw 10 from disassociating with one another. In this exemplary embodiment, the shaft 42 and handle 44 of the driver 40 are cannulated so that the passing suture 30 can be passed from one end of the driver 40 to the other through the interior of the driver 40. To facilitate wrapping of the passing suture 30, in this embodiment, the handle 44 of the driver 40 defines a spool. The intraosseous screw 10, passing suture 30, and driver 40 can thus be provided to surgeons in the above-described assembled form to improve surgical time efficiency by eliminating the need to load the passing suture 30 and driver 40 into the intraosseous screw 10.

Figure 6:
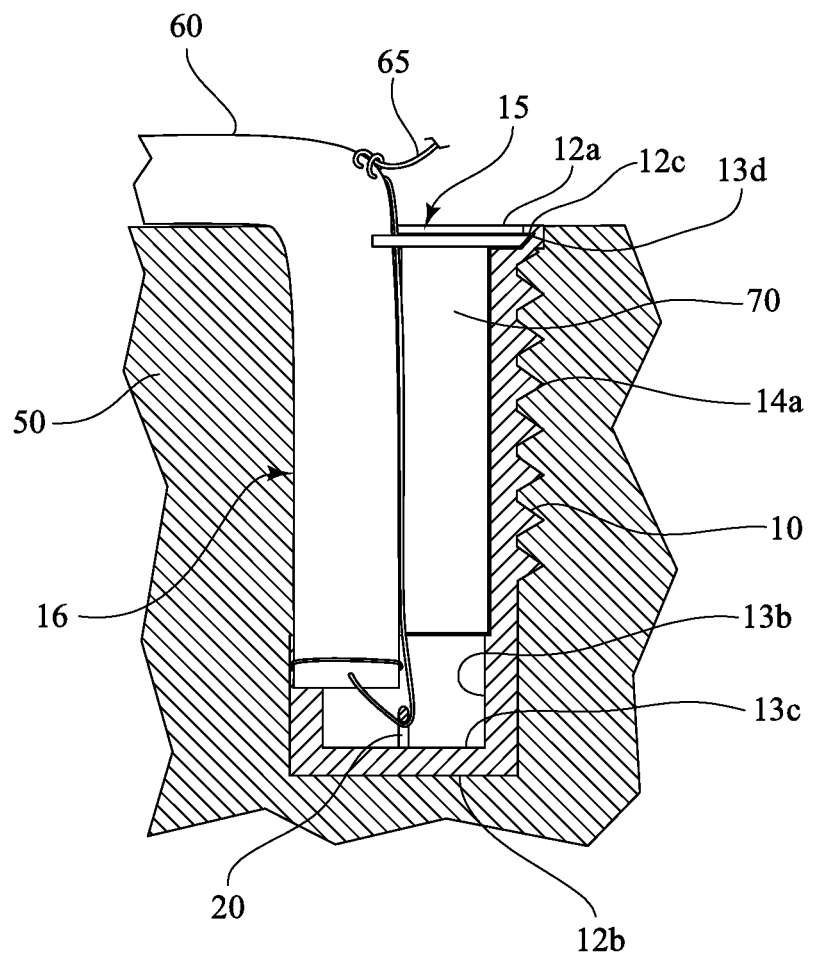
FIG. 6 is another sectional view of the exemplary intraosseous screw of FIG. 2 taken along line 5-5 similar to FIG. 5, but with the suture, soft tissue, and peg inserted within the axial cavity of the intraosseous screw.

FIGS. 5 and 6, respectively, show the intraosseous screw 10 deposited within the target bone structure 50 and the soft tissue 60 being loaded into the intraosseous screw 10. As shown in FIGS. 5 and 6, because of the axial cavity 15 provided within the intraosseous screw 10, the intraosseous screw 10 can be fully deposited within the target bone structure 50 prior to insertion of the soft tissue 60 into the target bone structure 50 and association of the soft tissue 60 with the intraosseous screw 10. To deposit the intraosseous screw 10 into the target bone structure 50, the intraosseous screw 10 is first aligned at the desired location along the target bone structure 50 and subsequently deposited therein. To facilitate purchase of the threading 14a and full deposit of the intraosseous screw 10 into the target bone structure 50, the driver 40 (shown in FIG. 4) is rotated in a rotational direction (e.g., clockwise) to apply the requisite torque necessary to drive the threading 14a, and thus the intraosseous screw 10 as a whole, into the target bone structure 50. The incisions within the target bone structure 50 which would be present due to the threading 14a of the intraosseous screw 10 have been omitted in FIGS. 5 and 6 to better illustrate certain features of the intraosseous screw 10 and the manner in which soft tissue 60 is able to engage the target bone structure 50 once loaded into the intraosseous screw 10. In some implementations, a surgically created bone tunnel or pilot hole may be created within the target bone structure 50 to facilitate initial insertion of the intraosseous screw 10.

Referring now to FIGS. 4-6, once the intraosseous screw 10 is fully deposited within the target bone structure 50, the driver 40 can be removed from the axial cavity 15 and disassociated from the intraosseous screw 10. To disassociate the driver 40 and the intraosseous screw 10, the passing suture 30 is unwrapped or untied from the driver 40 and the driver 40 is pulled away from the intraosseous screw 10 causing the passing suture 30 to travel through the cannulated handle 44 and shaft 42 of the driver 40. As the passing suture 30 is preloaded into the axial cavity 15 in the manner previously described, the passing suture 30 can be used to guide a suture 65 connected to soft tissue 60 into the axial cavity 15 and through the opening 22 of the intraosseous screw 10, as shown in FIG. 5. In this regard, one end of the passing suture 30 can be connected to the suture 65 connected to the soft tissue 60 and the other end of the passing suture 30 pulled to guide the suture 65 connected to the soft tissue 60 through the opening 22 until the soft tissue 60 is deposited in the axial cavity 15 of the intraosseous screw, as shown in FIG. 6. In this exemplary embodiment, the suture 65 connected to the soft tissue 60 is drawn through the opening 22 so that the soft tissue 60 nearly extends the full length of the axial cavity 15. Of course, the extent to which the soft tissue 60 is deposited into the axial cavity 15 may be adjusted as desired by adjusting the length of the suture 65 connected to the soft tissue 60 and the extent to which the suture 65 is pulled through the opening 22. Once the suture 65 connected to the soft tissue 60 is passed through the opening 22 of the intraosseous screw 10 and recovered, the passing suture 30 can be disconnected and discarded.

To ensure the soft tissue 60 is maintained within the axial cavity 15, the end of the suture 65 connected to the soft tissue 60 having passed through the opening 22 can be passed back through the soft tissue 60 and tied using stitching and/or suturing techniques known within the art, as shown in FIG. 6. Additionally or alternatively, the intraosseous screw 10 may further include a secondary retention member 24, 26, as further described below with reference to FIGS. 8 and 9, to which the suture 65 connected to the soft tissue 60 can be tied to after passing through the opening 22 to maintain the soft tissue 60 within the axial cavity 15. To prevent slippage of the soft tissue 60 from the axial cavity 15, it is generally preferred that the suture 65 connected to the soft tissue 60 be pulled taught before being tied to the soft tissue 60 and/or secondary retention member 24, 26. As shown in FIG. 6, even though the soft tissue 60 is deposited within the interior of the intraosseous screw 10, the soft tissue 60 is still able to contact the bony cortex of the target bone structure 50 through the window 16. The intraosseous screw 10 of the present disclosure permits the necessary contact between the soft tissue 60 and target bone structure 50 required for healing, but does so without requiring the soft tissue 60 to be interposed between the intraosseous screw 10 and bony cortex of the target bone structure 50. Accordingly, the intraosseous screw 10 can be fully deposited within the target bone structure 50 without the soft tissue 60 adversely affecting purchase of the threading 14*a* with the bony cortex of the target bone structure 50. Moreover, because the soft tissue 60 is deposited within the interior (axial cavity 15) of the intraosseous screw 10, as opposed to interposed between the exterior surface 14 of the screw and the bony cortex of the target bone structure 50, the risk of soft tissue 60 wrapping around the intraosseous screw 10 is eliminated. The foregoing features also enable the size of intraosseous screw 10 to be selected based on the dimensions of the intraosseous screw 10 alone, instead of having to account for both the dimensions of the intraosseous screw 10 and the soft tissue 60.

Figure 7:
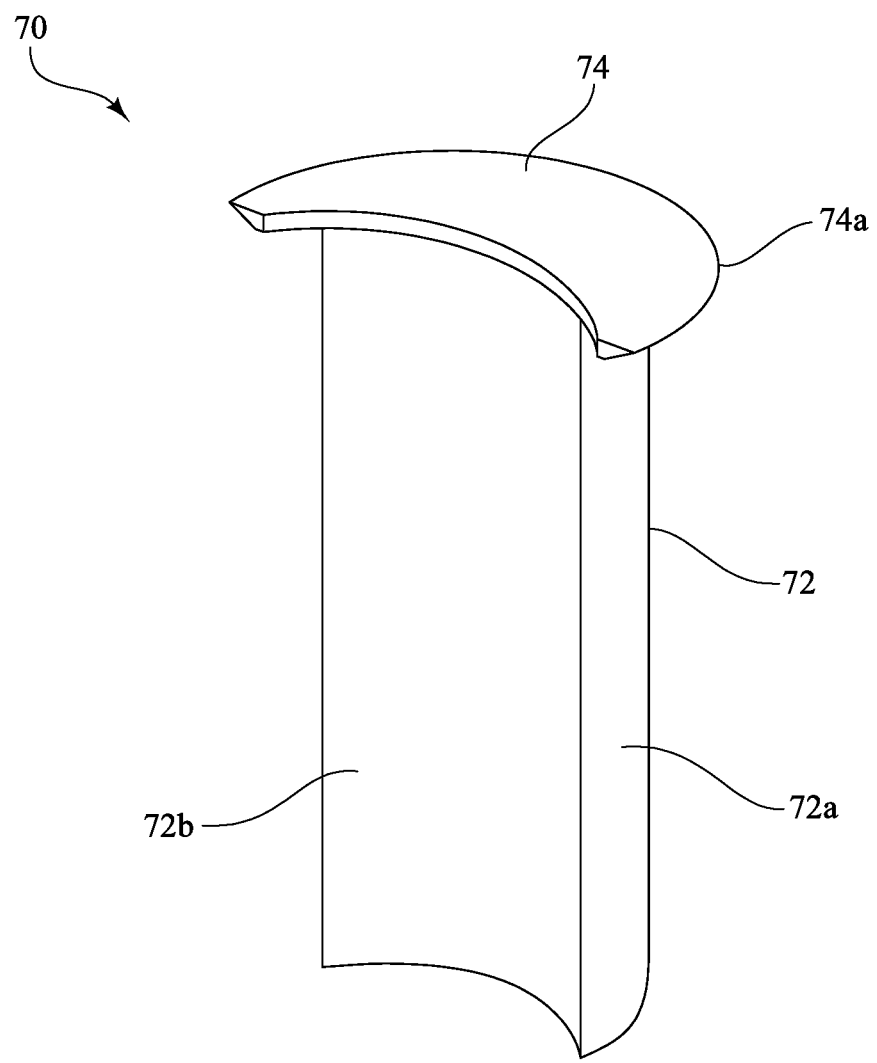
FIG. 7 is a perspective view of the peg of FIG. 5.

FIG. 7 shows a perspective view of a peg 70 which may optionally be utilized in combination with the intraosseous screw 10. Referring now to FIGS. 5-7, the peg 70 is configured for insertion into the axial cavity 15 to urge soft tissue 60 deposited therein towards the window 16 to promote contact between the soft tissue 60 and the target bone structure 50. As such, the peg 70 is useful in instances where soft tissue 60 deposited within the axial cavity 15 is undersized or the desired contact between the soft tissue 60 and the target bone structure 50 is otherwise not achieved by anchoring the soft tissue 60 within the axial cavity 15 alone. To urge the soft tissue 60 towards the window 16, the peg 70 is shaped to occupy a predefined volume of the axial cavity 15 when inserted therein. As perhaps best shown in FIGS. 6 and 7, in this exemplary embodiment, the peg 70 is shaped to occupy less than half of the total volume within the axial cavity 15. Of course, the size of the peg 70 may be adjusted to occupy more or less of the volume within the axial cavity 15 depending on the size of soft tissue 60 deposited within the axial cavity 15. Further, in this exemplary embodiment, the peg 70 is defined by and can be characterized as including a body 72 and a head 74. The body 72 has a first surface 72*a* which corresponds to an arc of the first portion 13*a* of the interior surface 13 and a second surface 72*b* which abuts the soft tissue 60 when the soft tissue 60 and peg 70 are both present within the axial cavity 15. In this exemplary embodiment, both the body 72 and the head 74 retain a generally crescent shape. The head 74 is oversized relative to both the body 72 of the peg 70 so that the head 74 is able to rest on the first shelf defined by the first portion 13*a* of the interior surface located below the rim 12*c*.

Referring now to FIGS. 1 and 3-7, in this exemplary embodiment, the interior surface 13 further defines a recess 13*d* within the axial cavity 15 located proximate the rim 12*c* of the body 12, which serves to maintain the peg 70 within the axial cavity 15 once inserted therein. The recess 13*d* defines an arc which corresponds to the arc defined by an outer edge 74*a* of the head 74 of the peg 70. The recess 13*d* resides along a plane which is substantially perpendicular to the plane along which the axial cavity 15 extends, as perhaps best shown in FIG. 3. The head 74 of the peg 70 is oversized relative to the inlet defined by the rim 12*c* of the body 12, such that the head 74 and/or body 12 of the intraosseous screw 10 must temporarily deform to permit the outer edge 74*a* to travel past the inlet defined by the rim 12*c*. In this regard, at least the head 74 of the peg 70 is constructed of a plastic material, such as PEEK. The recess 13*d* has a depth which permits the outer edge 74*a* of the head 74 to be seated therein when the head 74 driven past the inlet defined by the rim 12*c*. In this way, the peg 70 can be "snapped" into a fixed position within the axial cavity 15. The recess 13*d* preferably extends the length of the rim 12*c* to accommodate pegs 70 with heads 74 having an outer edge 74*a* with different arc lengths.

Figure 8:
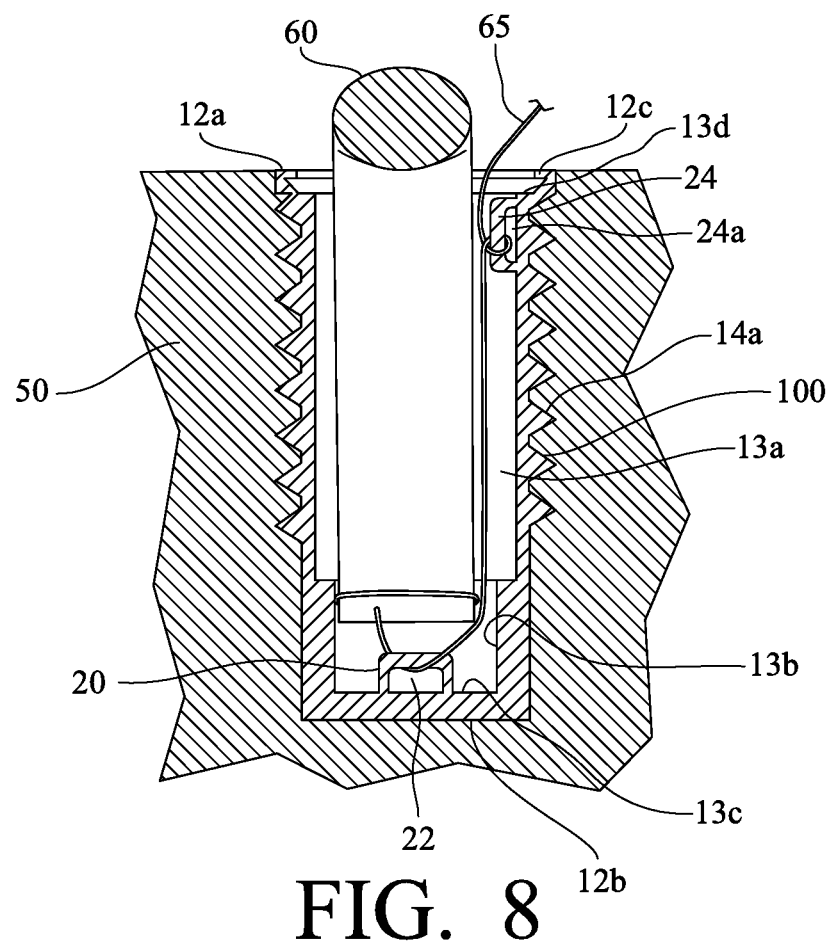
FIG. 8 is a sectional view of another exemplary intraosseous screw made in a accordance with the present invention deposited within a bone structure, with a suture and soft tissue inserted in the axial cavity of the intraosseous screw.
Figure 9:
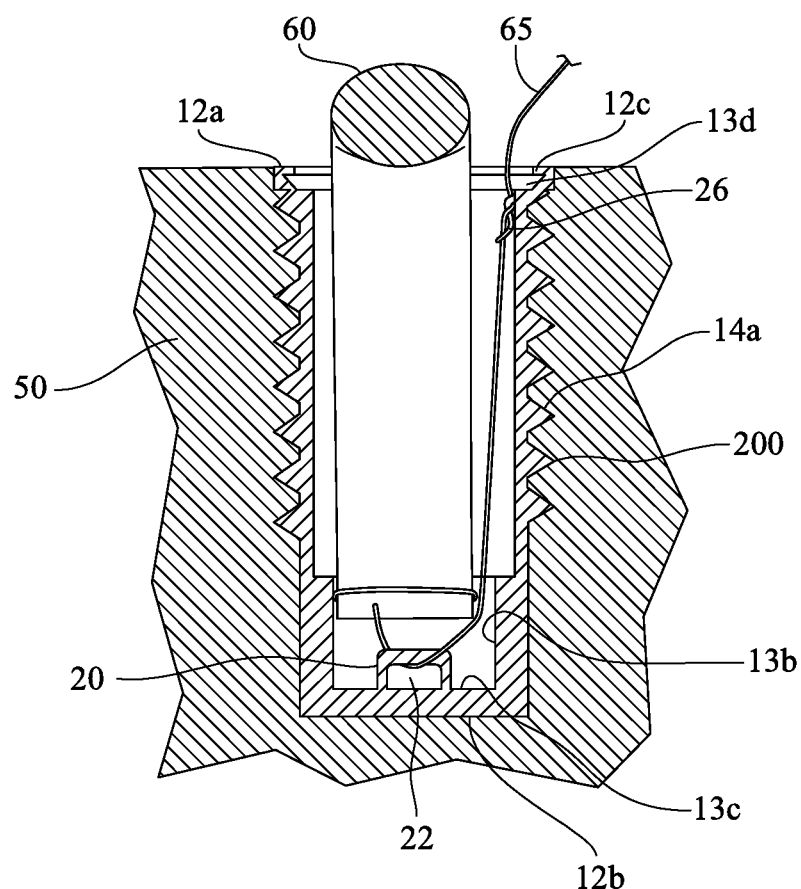
FIG. 9 is a sectional view of another exemplary intraosseous screw made in accordance with the present invention deposited within a bone structure, with a suture and soft tissue inserted in the axial cavity of the intraosseous screw.

Referring now to FIGS. 8 and 9, as a further refinement, the exemplary intraosseous screw 10 may further optionally include a secondary retention member 24, 26 to which the suture 65 connected to the soft tissue 60 can be tied instead of or in addition to the soft tissue 60 after passing through the opening 22 to maintain the soft tissue 60 within the axial cavity 15. The secondary retention member 24, 26 is positioned above (i.e., closer to the proximal end 12*a* of the body) the retention member 20 described above.

Referring now specifically to FIG. 8, another exemplary intraosseous screw 100 is shown. The exemplary intraosseous screw 100 shown in FIG. 8 provides the same functionality and includes the same features as the intraosseous screw 10 described above with reference to FIGS. 1-6, except, in this embodiment, the intraosseous screw 100 further includes a secondary retention member comprised of an arced structure 24. The arced structure 24 is positioned within the axial cavity 15 proximate to the inlet and is enclosed by the first portion 13*a* of the interior surface 13. In this exemplary embodiment, the arced structure 24 is defined by the body 12 of the intraosseous screw 100 and extends outwardly from the first portion 13*a* of the interior surface 13 within the axial cavity 15. As such, the combination of the arced structure 24 and the first portion 13*a* of the interior surface 13 thus define another opening 24*a* through which the suture 65 connected to the soft tissue 60 can pass to facilitate tying of the suture 65 to the arced structure 24.

Referring now specifically to FIG. 9, another exemplary intraosseous screw 200 is shown. The exemplary intraosseous screw 200 shown in FIG. 9 provides the same functionality and includes the same features as the intraosseous screw 10 described above with reference to FIGS. 1-6, except, in this embodiment, the intraosseous screw 200 includes a secondary retention member comprised of a cleat 26 to which the suture 65 connected to the soft tissue 60 can be wrapped and tied. In this exemplary embodiment, the cleat 26 is positioned within the axial cavity 15 on the proximal end 12*a* of the body 12. In this exemplary embodiment, the cleat 26 is defined by the body 12 of the intraosseous screw 10 and extends outwardly from the first portion 13*a* of the interior surface 13.

Figure 10:
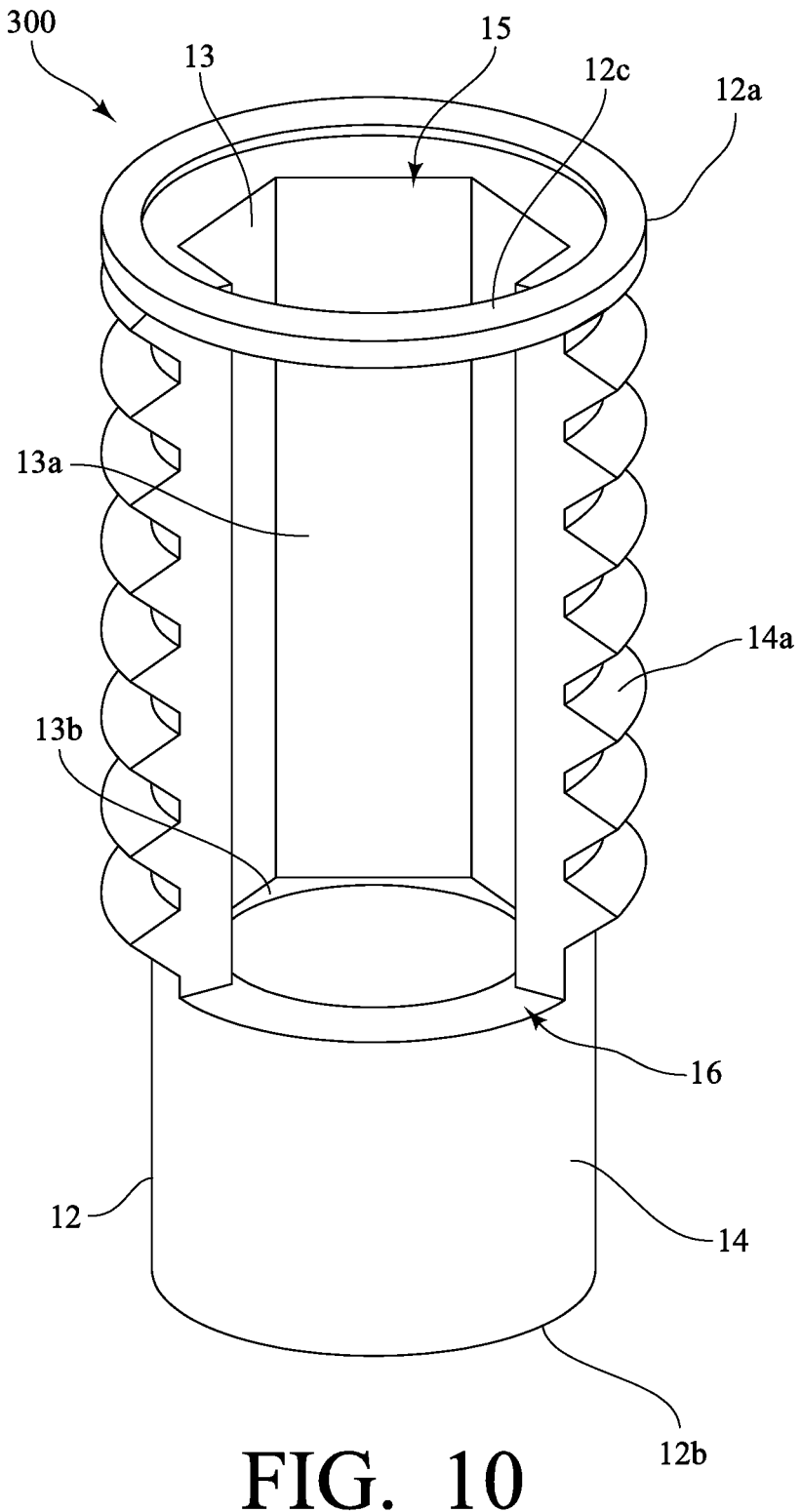
FIG. 10 is a perspective view of another exemplary intraosseous screw made in accordance with the present invention.

Referring now to FIG. 10, another exemplary intraosseous screw 300 made in accordance with the present invention is shown. The exemplary intraosseous screw 300 shown in FIG. 10 provides the same functionality and includes the same features as the intraosseous screw 10 described to above with reference to FIGS. 1-6, except that the rim 12*c* defining the inlet is continuous (i.e., unbroken), such that the window 16 is fully enclosed by the body 12 of the intraosseous screw 300. The additional material in the rim 12*c* may serve to improve the structural integrity of the intraosseous screw 300 with regards to the application of torque while still providing a window 16 which can facilitate contact between a soft tissue 60 deposited within the intraosseous screw 300 and at target bone structure 50.

Figure 11:
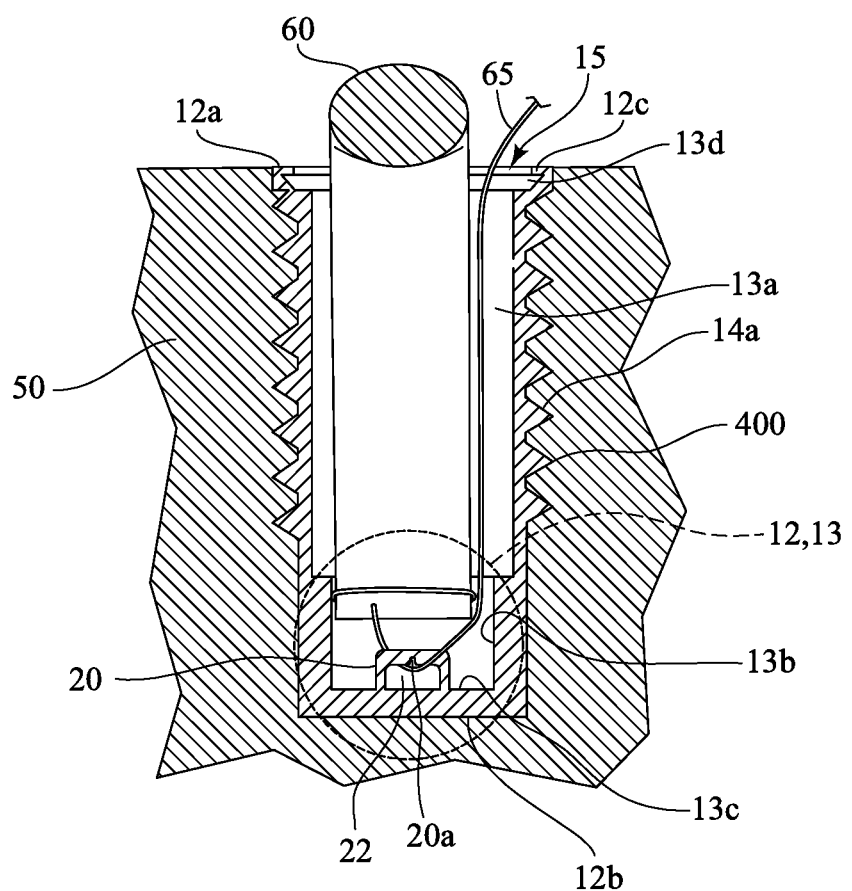
FIG. 11 is a sectional view of another exemplary intraosseous screw made in accordance with the present invention deposited within a bone structure, with a suture and soft tissue inserted in the axial cavity of the intraosseous screw.
Figure 12:
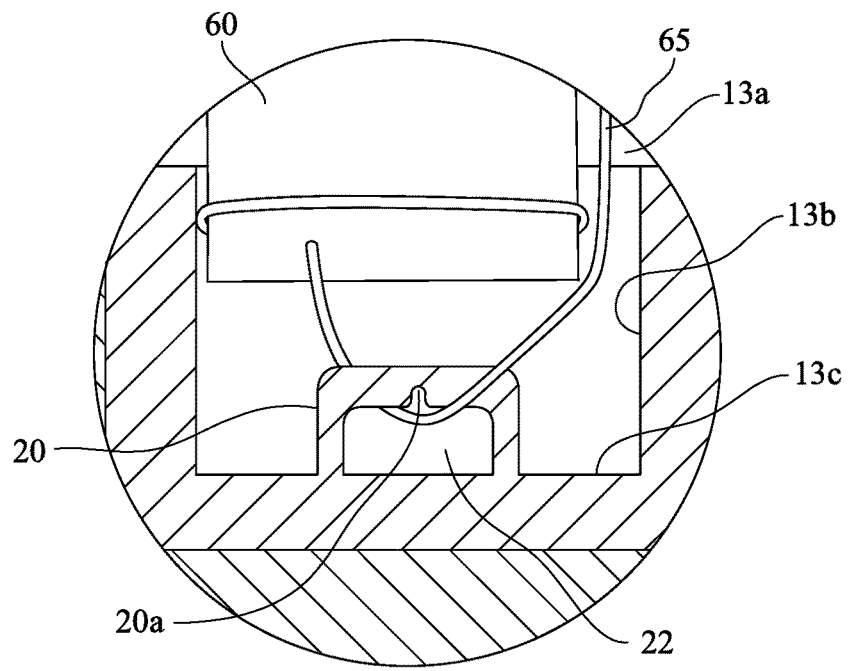
FIG. 12 is a magnified partial view of the intraosseous screw of FIG. 11.
Figure 13:
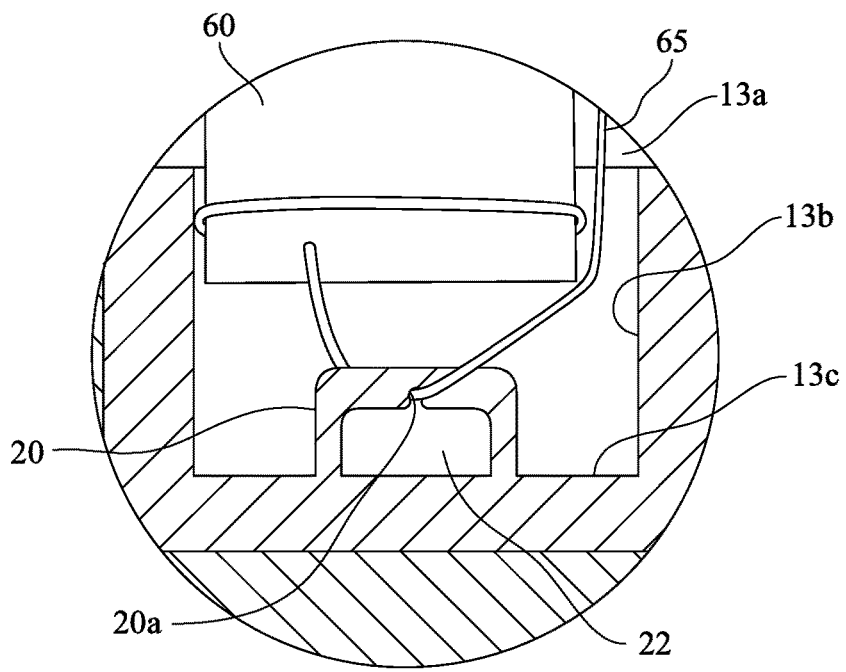
FIG. 13 is another magnified partial view of the intraosseous screw of FIG. 11 similar to FIG. 12, but with the suture connected to the soft tissue deposited within a slot of the retention member of the intraosseous screw.

Referring now to FIGS. 11-13, another exemplary intraosseous screw 400 made in accordance with the present invention is shown. The exemplary intraosseous screw 400 shown in FIGS. 11-13 provides the same functionality and includes the same features as the intraosseous screw 10 as described above with reference to FIGS. 1-6, except that the retention member 20 defines and can be characterized as including a slot 20*a* configured to receive the suture 65 connected to the soft tissue 60. Preferably, the dimensions of the channel defined by the slot 20*a* are such that, when the suture 65 connected to the soft tissue 60 is pulled into the slot 20a, the slot 20a imposes a pinching force upon the suture 65 that prevents the suture 65 from dislodging therefrom. In some embodiments, the dimensions of the slot 20a may be adjusted at the time of manufacture to impose a pinching force sufficient to limit or prevent the suture 65 connected to the soft tissue 60 from in advertently back traveling through the opening 22 once the suture 65 is deposited within the tapered slot. In this way, once the suture 65 connected to the soft tissue 60 is deposited the desired amount within the axial cavity 15, the suture 65 connected to the soft tissue 60 can be pulled into the slot 20a to further maintain the soft tissue 60 within the axial cavity 15, as evidenced by viewing FIGS. 12 and 13 in sequence.

The dimensions of the intraosseous screw 10, 100, 200, 300, 400 can be adjusted at the time of manufacture to accommodate different surgical applications, bone structures, and/or soft tissue sizes. For instance, a larger size intraosseous screw may be required for bicep tenodesis in the proximal humerus, whereas a smaller of the intraosseous screw may be required for distal bicep repair, and an even smaller intraosseous screw required for tendon repair in the hand or the foot. Accordingly, the intraosseous screw 10, 100, 200, 300, 400 may be provided in a variety of diameters and lengths. To accommodate most tenodesis grafts, in some embodiments, the diameter of the intraosseous screw 10, 100, 200, 300, 400 may range from approximately 3 mm to approximately 9 mm, and the length of the intraosseous screw 10, 100, 200, 300, 400 may range from approximately 8 mm to approximately 23 mm.

The material from which the intraosseous screw 10, 100, 200, 300, 400 is constructed may similarly vary depending on the intended application, target bone structure, and/or soft tissue size. As such, the intraosseous screw 10, 100, 200, 300, 400 may be constructed of a variety materials currently known and utilized within the art including: thermoplastics, such as PEEK; metals, such as titanium; and biocomposite materials. Construction of the intraosseous screw 10, 100, 200, 300, 400 can be achieved using suitable additive and/or subtractive manufacturing methods known in the art.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An intraosseous screw for deposit into a bone structure and retaining a soft tissue therein, comprising:
    a body defining a longitudinal axial cavity for receiving the soft tissue, such that the soft tissue can be deposited longitudinally within the axial cavity, and a window for permitting the soft tissue to directly contact the bone structure at the time the soft tissue is deposited within the axial cavity and subsequent to the intraosseous screw being deposited in the bone structure, the body including
        an open proximal end providing entry into the axial cavity,
        a closed distal end, and
        an exterior surface including threading for engaging the bone structure; and
    a retention member positioned within the axial cavity below the window, the retention member at least partially defining an opening configured to permit passage of a suture connected to the soft tissue therethrough;
    wherein the window extends more than half of a total length of the body.

2. The intraosseous screw according to claim 1, wherein the proximal end includes a rim and the window extends from the rim towards the distal end, such that the rim is noncontinuous.

3. The intraosseous screw according to claim 1, wherein at least a portion of an interior surface of the body is configured to mate with a driver for depositing the intraosseous screw into the bone structure.

4. The intraosseous screw according to claim 3, wherein the interior surface includes a first portion configured to mate with a shaft of the driver and a second portion defining a circumferential shelf surrounding the retention member.

5. The intraosseous screw according to claim 3, wherein the interior surface is configured to mate with a hexagonally shaped shaft of the driver.

6. The intraosseous screw according to claim 1, wherein the retention member extends from a base of the axial cavity towards the proximal end.

7. The intraosseous screw according to claim 1, wherein the retention member is defined by the body.

8. The intraosseous screw according to claim 1, wherein the retention member includes a slot configured to receive the suture.

9. The intraosseous screw according to claim 1, wherein a width of the window is equal to approximately one-fourth to one-half of a circumference of the body.

10. The intraosseous screw according to claim 1, further comprising:
    a secondary retention member to which the suture can be tied after passing through the opening.

11. An intraosseous screw for deposit into a bone structure and retaining a soft tissue therein, comprising:
    a body defining a longitudinal axial cavity for receiving the soft tissue, such that the soft tissue can be deposited longitudinally within the axial cavity, and a window for permitting the soft tissue to directly contact the bone structure at the time the soft tissue is deposited within the axial cavity and subsequent to the intraosseous screw being deposited in the bone structure, the body including
        an open proximal end providing entry into the axial cavity,
        a closed distal end, and
        an exterior surface including threading for engaging the bone structure; and
    a retention member positioned within the axial cavity below the window, the retention member at least partially defining an opening configured to permit passage of a suture connected to the soft tissue therethrough;
    wherein an interior surface of the body defines a recess within the axial cavity for receiving a peg configured for insertion into the axial cavity to fill a pre-defined volume of the axial cavity and laterally urge soft tissue deposited within the axial cavity towards the window; and
    wherein the recess resides along a first plane substantially perpendicular to a second plane along which the axial cavity extends.

12. A system for associating a soft tissue with a bone structure, comprising:
    an intraosseous screw, the intraosseous screw including
        a body defining a longitudinal axial cavity for receiving the soft tissue, such that the soft tissue can be deposited longitudinally within the axial cavity, and a window for permitting the soft tissue to directly contact the bone structure at the time the soft tissue is deposited within the axial cavity and subsequent to the intraosseous screw being deposited in the bone structure, the body including
an open proximal end providing entry into the axial cavity,
a closed distal end, and
an exterior surface including threading for engaging the bone structure, and
a retention member positioned within the axial cavity below the window, the retention member at least partially defining an opening; and
a passing suture for guiding a suture connected to the soft tissue through the opening, the passing suture having a first end and a second end and extending through the opening, such that the first end and the second end are each positioned outside of the axial cavity;
wherein the window extends more than half of a total length of the body of the intraosseous screw.

13. The system according to claim 12, and further comprising;
a driver for depositing the intraosseous screw into the bone structure, the driver including a cannulated shaft at least partially deposited within the axial cavity.

14. The system according to claim 13, wherein the passing suture extends through the cannulated shaft, such that the passing suture can be wound around a handle of the driver to prevent the shaft and the intraosseous screw from disassociating therewith.

15. A system for associating a soft tissue with a bone structure, comprising:
an intraosseous screw, the intraosseous screw including
a body defining a longitudinal axial cavity for receiving the soft tissue and a window for permitting the soft tissue to contact the bone structure while deposited within the axial cavity, the body including
an open proximal end providing entry into the axial cavity,
a distal end, and
an exterior surface including threading for engaging the bone structure, and
a retention member positioned within the axial cavity below the window, the retention member at least partially defining an opening configured to permit passage of a suture connected to the soft tissue therethrough; and
a peg configured for insertion into the axial cavity, the peg being shaped to fill a predefined volume of the axial cavity and such that, when the soft tissue is deposited within the axial cavity and the peg is inserted into the axial cavity, the peg laterally urges the soft tissue towards the window.

16. The system according to claim 15, wherein the peg includes an elongated body and a head extending perpendicular to the body, and wherein an interior surface of the body defines a recess within the axial cavity for receiving an outer edge of the head.

17. A method for associating a soft tissue with a bone structure, comprising:
depositing an intraosseous screw into the bone structure, the intraosseous screw including
a body defining a longitudinal axial cavity for receiving the soft tissue, such that the soft tissue can be deposited longitudinally within the cavity, and a window for permitting the soft tissue to directly contact the bone structure at the time the soft tissue is deposited within the axial cavity and subsequent to the intraosseous screw being deposited in the bone structure, the body including
an open proximal end providing entry into the axial cavity,
a closed distal end, and
an exterior surface including threading for engaging the bone structure, and
a retention member positioned within the axial cavity below the window, the retention member at least partially defining an opening configured to permit the passage of a suture connected to the soft tissue therethrough; and
anchoring the soft tissue within the axial cavity of the intraosseous screw following deposit of the intraosseous screw into the bone structures;
wherein the window extends more than half of a total length of the body of the intraosseous screw.

18. The method according to claim 17, wherein anchoring the soft tissue to the retention member includes passing the suture connected to the soft tissue through the opening.

19. The method according to claim 18, further comprising the step of inserting a peg into the axial cavity to urge the soft tissue towards the window.

20. The method according to claim 18, wherein anchoring the soft tissue to the retention member includes tying the suture to at least one of the soft tissue and a secondary retention member of the intraosseous screw.

* * * * *